United States Patent [19]

White

[11] 4,149,404
[45] Apr. 17, 1979

[54] PRESSURE TESTING OF ROCKET MOTOR CASES

[75] Inventor: Niles C. White, Huntsville, Ala.

[73] Assignee: The United States of America as represented by the Secretary of the Army, Washington, D.C.

[21] Appl. No.: 909,071

[22] Filed: May 24, 1978

[51] Int. Cl.² .......................................... G01M 15/00
[52] U.S. Cl. .......................................... 73/49.7; 73/37
[58] Field of Search ............... 73/49.7, 37, 52, 118, 73/116; 60/253

[56] References Cited

U.S. PATENT DOCUMENTS 3,329,799  7/1967  Carmody .......................... 73/118
3,377,841  4/1968  Neal .................................. 73/49.7

FOREIGN PATENT DOCUMENTS 1369194  6/1964  France ............................... 60/253

*Primary Examiner*—S. Clement Swisher
*Assistant Examiner*—Denis E. Corr
*Attorney, Agent, or Firm*—Nathan Edelberg; Robert P. Gibson; James T. Deaton

[57] ABSTRACT

A method for pressure testing a rocket motor case by inserting a movable piston in the nozzle end of the rocket motor case, sealing the piston relative to the throat of the rocket motor case and then applying pressure to the rocket motor case to pressure test the rocket motor case to a predetermined pressure or to failure.

2 Claims, 1 Drawing Figure

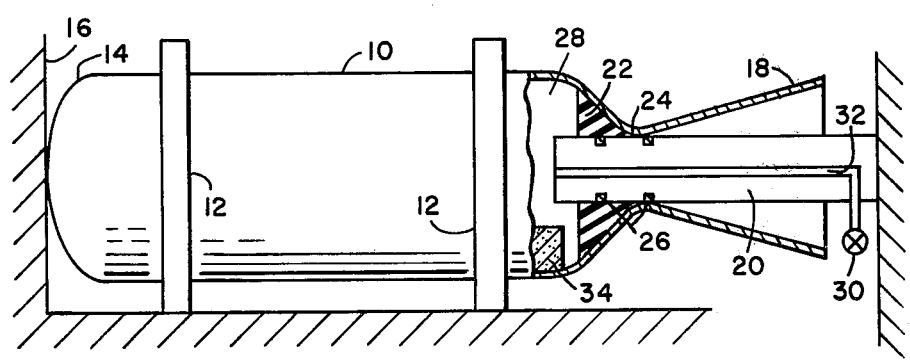

PRESSURE TESTING OF ROCKET MOTOR CASES

DEDICATORY CLAUSE

The invention described herein may be manufactured, used, and licensed by or for the Government for governmental purposes without the payment to me of any royalties thereon.

BACKGROUND OF THE INVENTION

Stress distribution in rocket motor cases is quite complex and simple stress analysis though useful can hardly be accurate. For this reason, as well as because of the low safety factors which must be used to save weight in the rocket motor cases, any rocket motor case design must be thoroughly tested. Hydrostatic testing and propellant pressurization have been found useful in control of the rocket motor case design and in control of production acceptance criteria for the rocket motor case. Rocket motor cases are generally tested to some pressure above normal operating pressure. Known methods include the nozzle being plugged and water inserted into the rocket motor case and a load applied to the rocket motor case to meet the specified psi load. This type of text puts an increased load on the nozzle end since the area is increased by the area of the throat ($A_T$) and since the force is the pressure times the area ($A_T$). Therefore, there is a need for a method which more accurately duplicates and actual motor test as if the rocket motor case were being tested under actual burning of rocket motor propellant within the rocket motor case.

Therefore, it is an object of this invention to provide a method by which a rocket motor case can be tested as near as possible under actual burning pressure application to the rocket motor case.

Another object of this invention is to provide a method for testing a rocket motor case in which the rocket motor case can be pressurized from an external source or by an internal source from burning of propellant within the rocket motor case.

Still another object of this invention is to equally distribute the pressure applied in the rocket motor case as it is distributed on actual burning of propellant with the rocket nozzle open as a exhaust.

Other objects and advantages of this invention will be obvious to those skilled in this art.

SUMMARY OF THE INVENTION

In accordance with this invention, a method for pressure testing rocket motor cases is provided that includes mounting the rocket motor case in space with one end of the motor case secured against actual movement in one direction and an opposite end of the motor case that has a nozzle having a piston inserted therethrough with the piston being sealed by an insert and grease relative to the throat of the nozzle so that any pressure exerted over the nozzle throat area will be exerted over the movable piston rather than the rocket motor case itself. This method of testing the rocket motor case allows fluid pressure to be externally communicated into the motor case to pressurize it or by igniting propellant within the motor case to provide the pressure. In this particular arrangement, the actual forces that the rocket motor case would experience in actual firing are exerted on the motor case to give actual motor firing test parameter without actually having to mount the motor case and completely fire a full round of propellant in the motor case. That is, any propellant used in the rocket motor case to pressurize it has a surface area and burning time to duplicate pressure test conditions under actual firing of a full round of propellant in the rocket motor case. With applicant's arrangement, the piston inserted through the throat area of the nozzle absorbs the pressure that would normally be exerted out the nozzle. As can be seen, the forces applied to the movable piston are not exerted on the rocket motor case since the movable piston is movable relative to the rocket motor case.

BRIEF DESCRIPTION OF THE DRAWING

The single FIGURE of the drawing is a schematic view partially cut away and in section of a rocket motor case in a test set up in accordance with this invention.

DESCRIPTION OF THE PREFERRED EMBODIMENT

Referring now to the drawing, a rocket motor case 10 that is desired to be tested is mounted in space by supports 12 against radial movement and at one end 14 by rigid support 16 yo prevent lateral movement of the rocket motor case in one direcion and a nozzle 18 at the other end of the rocket motor case has a movable piston 20 inserted therein with an insert 22, grease 24 and O-rings 26 for sealing piston 20 relative to the throat of nozzle 18. Fluid pressure can be applied to chamber 28 of rocket motor case 10 through valve 30 and passage means 32 or by a propellant charge 34 within rocket motor case 10. If the external pressurization system is used, the rocket motor case will probably not have propellant therein and if a propellant is used inside the rocket motor case to provide the pressurization thereof, the solid propellant will be ignited in a conventional manner and passage 32 will be closed by valve 30 or piston 20 will be solid with no passage 32.

In carrying out the method, the rocket motor case is mounted in the rigid supports as illustrated and the piston and seals are inserted in place so as to seal the throat of exhaust nozzle 18. With piston 20 sealed relative to exhause nozzle 18, chamber 28 of the rocket motor case is pressurized by introducing fluid pressure through valve 30 and passage 32 or by igniting propellant 34. The pressure applied in chamber 28 can be a predetermined amount to test the rocket motor case to a predetermined pressurized environment or the pressure can be applied until rupture of the motor case occurs. With applicant's specific arrangement, the pressure within chamber 28 exerts its force radially and actually on the motor case just as it would in actual flight. That is, the pressure that would be exhausted out exhaust nozzle 18 is transmitted to piston 20 and is not brought to bear on the rocket motor case itself as in systems in which the throat of the exhaust nozzle is plugged. With this arrangement, a true test of the rocket motor case can be made.

I claim:

1. A method for pressure testing a rocket motor case comprising: mounting a rocket motor case that has a chamber and a nozzle at one end of the chamber so that the rocket motor case is suspended against radial movement and axial movement in one direction, inserting a piston into the nozzle of said rocket motor case, sealing said piston relative to a throat of said nozzle so that said piston is movable relative to said throat when sealed, and pressurizing said rocket motor case by propellant within the rocket motor case to pressure test the rocket motor case.

2. A method for pressure testing a rocket motor case as set forth in claim 1, wherein said piston is sealed relative to said throat by an insert around said piston, by grease between said insert and a portion of said throat and by O-ring sealing means on said piston.

* * * * *